US009878337B1

(12) United States Patent
Hong

(10) Patent No.: US 9,878,337 B1
(45) Date of Patent: Jan. 30, 2018

(54) SPRAYER

(71) Applicant: SMBURE CO., LTD., Gwangju (KR)

(72) Inventor: Gi Sool Hong, Gwangju (KR)

(73) Assignee: SMBURE CO., LTD., Gwangju (KR)

( * ) Notice: Subject to any disclaimer, the term of this patent is extended or adjusted under 35 U.S.C. 154(b) by 0 days.

(21) Appl. No.: 15/360,963

(22) Filed: Nov. 23, 2016

(30) Foreign Application Priority Data

Sep. 19, 2016 (KR) ........................ 10-2016-0119039

(51) Int. Cl.

| | |
|---|---|
| ***B05B 7/00*** | (2006.01) |
| ***B05B 7/24*** | (2006.01) |
| ***B05B 15/00*** | (2006.01) |
| ***B05B 1/18*** | (2006.01) |
| ***B05B 12/00*** | (2006.01) |
| ***B05B 15/06*** | (2006.01) |
| *A61L 2/18* | (2006.01) |
| *A61L 2/22* | (2006.01) |

(52) U.S. Cl.

CPC .............. *B05B 7/2464* (2013.01); *B05B 1/18* (2013.01); *B05B 7/0075* (2013.01); *B05B 7/0081* (2013.01); *B05B 12/002* (2013.01); *B05B 15/008* (2013.01); *B05B 15/061* (2013.01)

(58) Field of Classification Search

CPC ... B05B 7/0075; B05B 7/0081; B05B 7/2416; B05B 7/2464; B05B 12/002; B05B 15/008; B05B 15/061; A01M 7/0003; A01M 7/0017; A01M 7/0021; A01M 7/0025; A01M 7/0032; A01M 7/0046; A61L 2/18; A61L 2/22; A61L 9/14; A61M 11/02

See application file for complete search history.

(56) References Cited

U.S. PATENT DOCUMENTS

| | | | | |
|---|---|---|---|---|
| 2,325,112 A * | 7/1943 | Constantine | B05B 7/2435 | 239/127 |
| 7,178,743 B2 * | 2/2007 | Clarke, III | B05B 7/2416 | 239/304 |
| 2011/0259978 A1 * | 10/2011 | Ptak | B05B 7/0416 | 239/398 |

FOREIGN PATENT DOCUMENTS

| | | |
|---|---|---|
| KR | 10-1079206 B1 | 11/2011 |
| KR | 10-1153188 B1 | 6/2012 |
| KR | 10-1185064 B1 | 9/2012 |

* cited by examiner

*Primary Examiner* — Darren W Gorman

(57) ABSTRACT

A sprayer includes a body which has a neck, of which an inner sectional area becomes gradually smaller as it goes towards a front side, on a front side of the blower module assembly, a chemical container that includes a chemical container top which has a check valve in the interior thereof, and a chemical discharge hole that is formed at a lower portion thereof, a blower module that is installed in the blower module assembly such that exterior air passes through the neck, a feeding pump that is connected to the chemical discharge hole by a connection pipe, an ejection nozzle assembly that connected to the feeding pump by a connection pipe, and a tube-shaped fixing cap are separated from and coupled to an end of the neck of the body.

12 Claims, 14 Drawing Sheets

【FIG. 1】
[Prior Art]
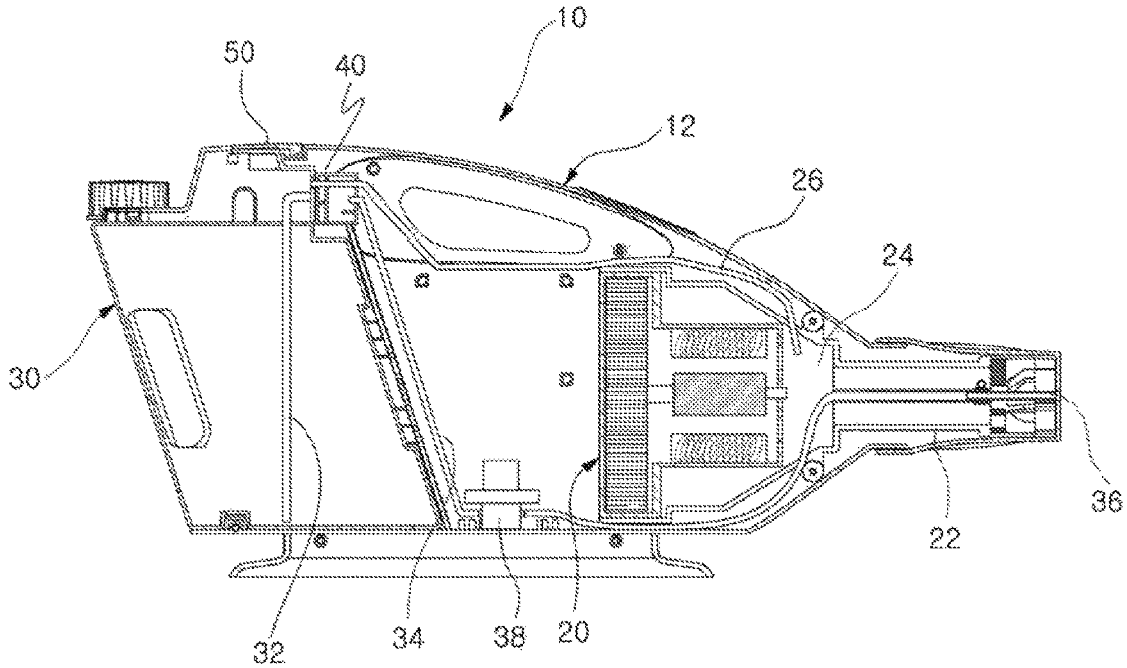

【FIG. 2】
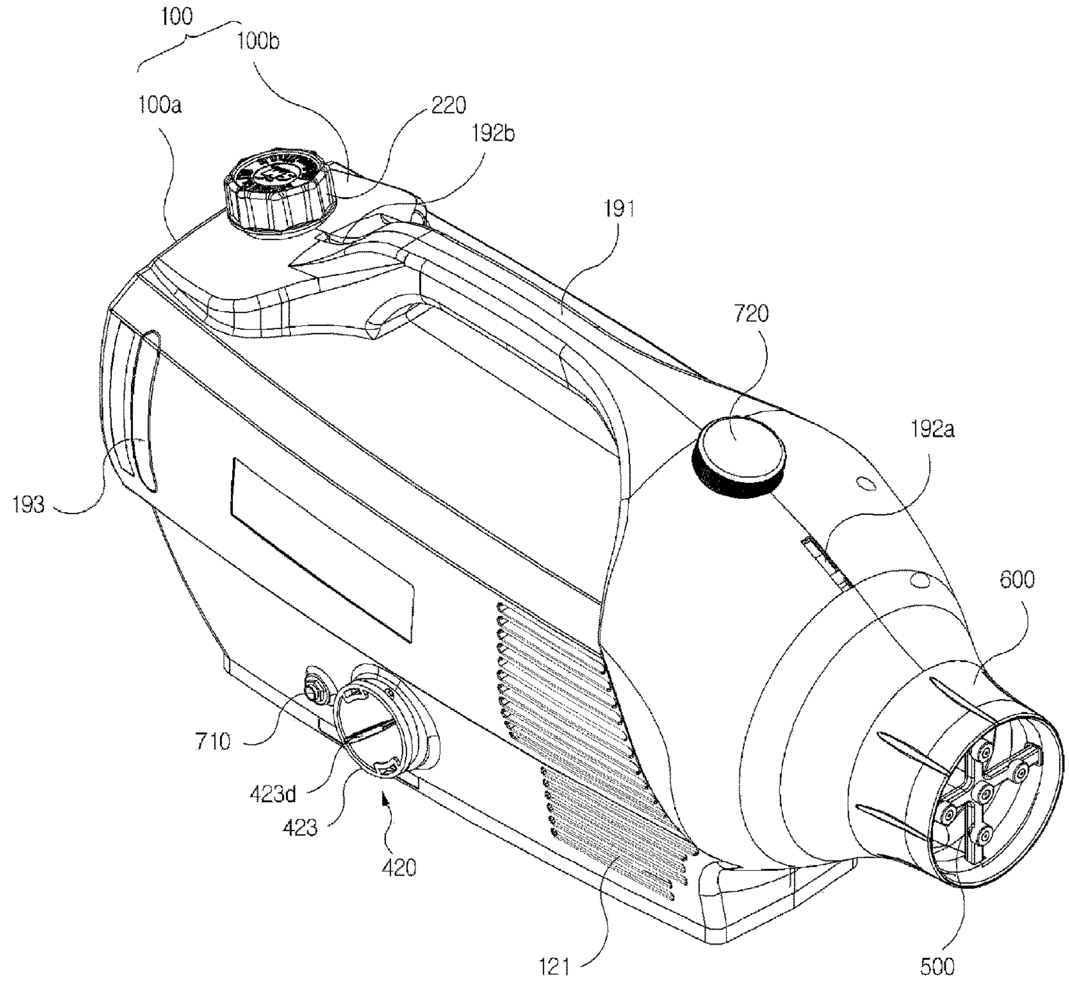

【FIG. 3】
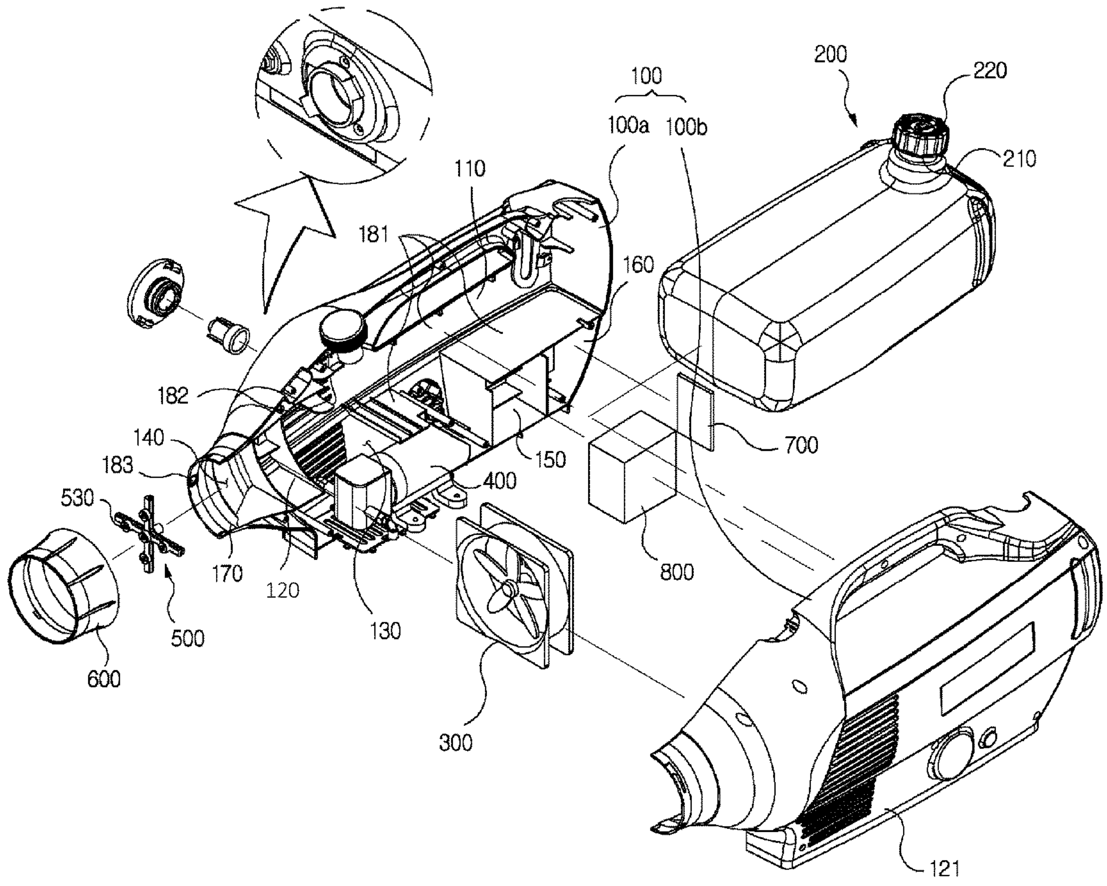

【FIG. 4】
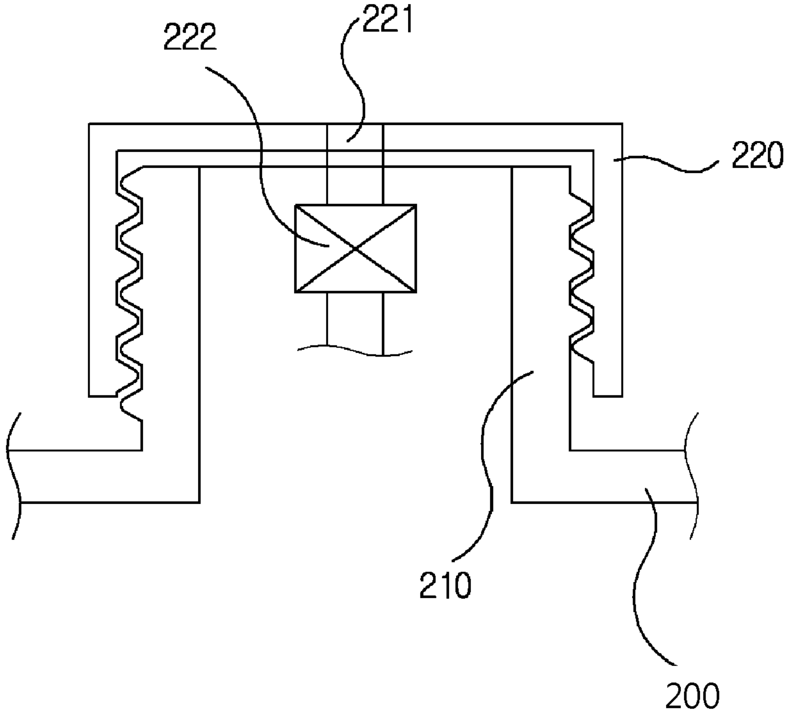

【FIG. 5A】
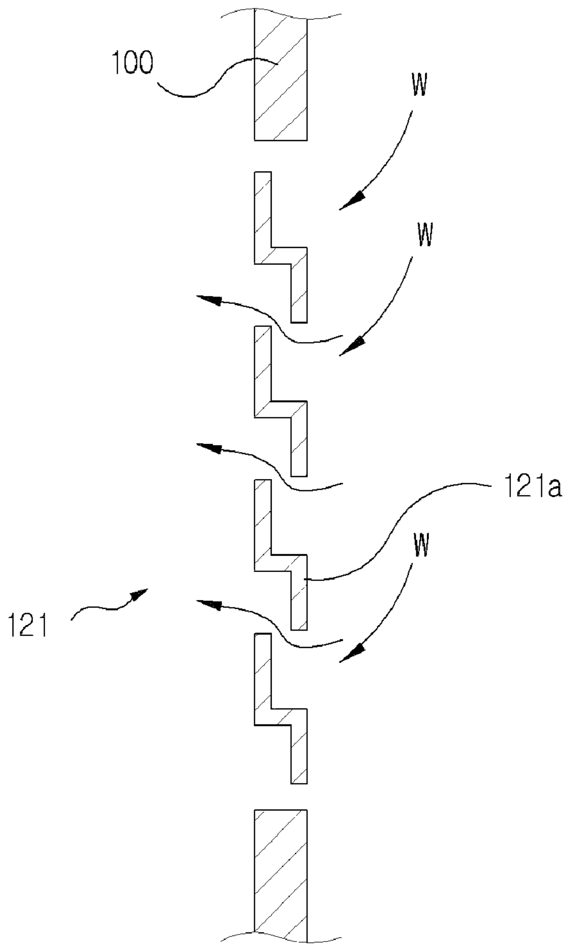

【FIG. 5B】
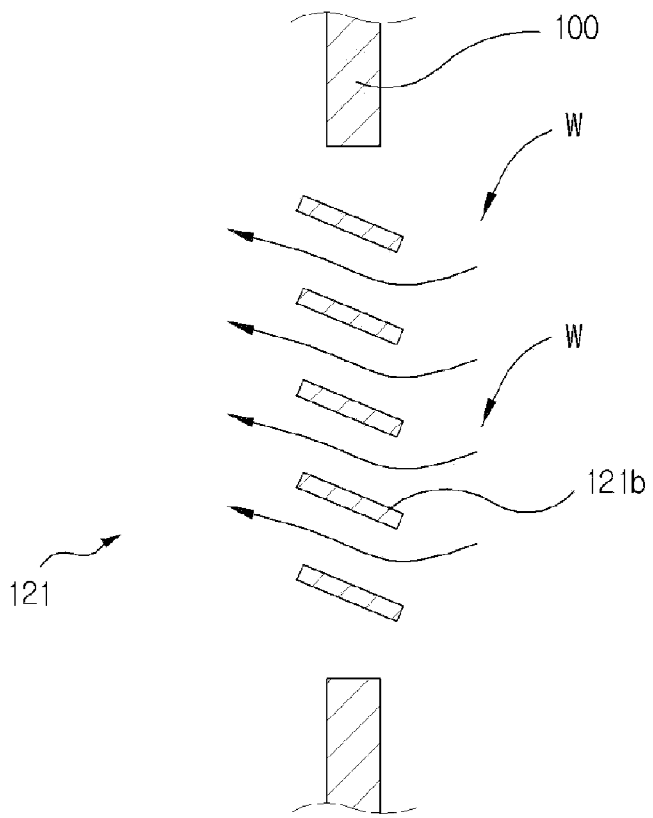

【FIG. 6】
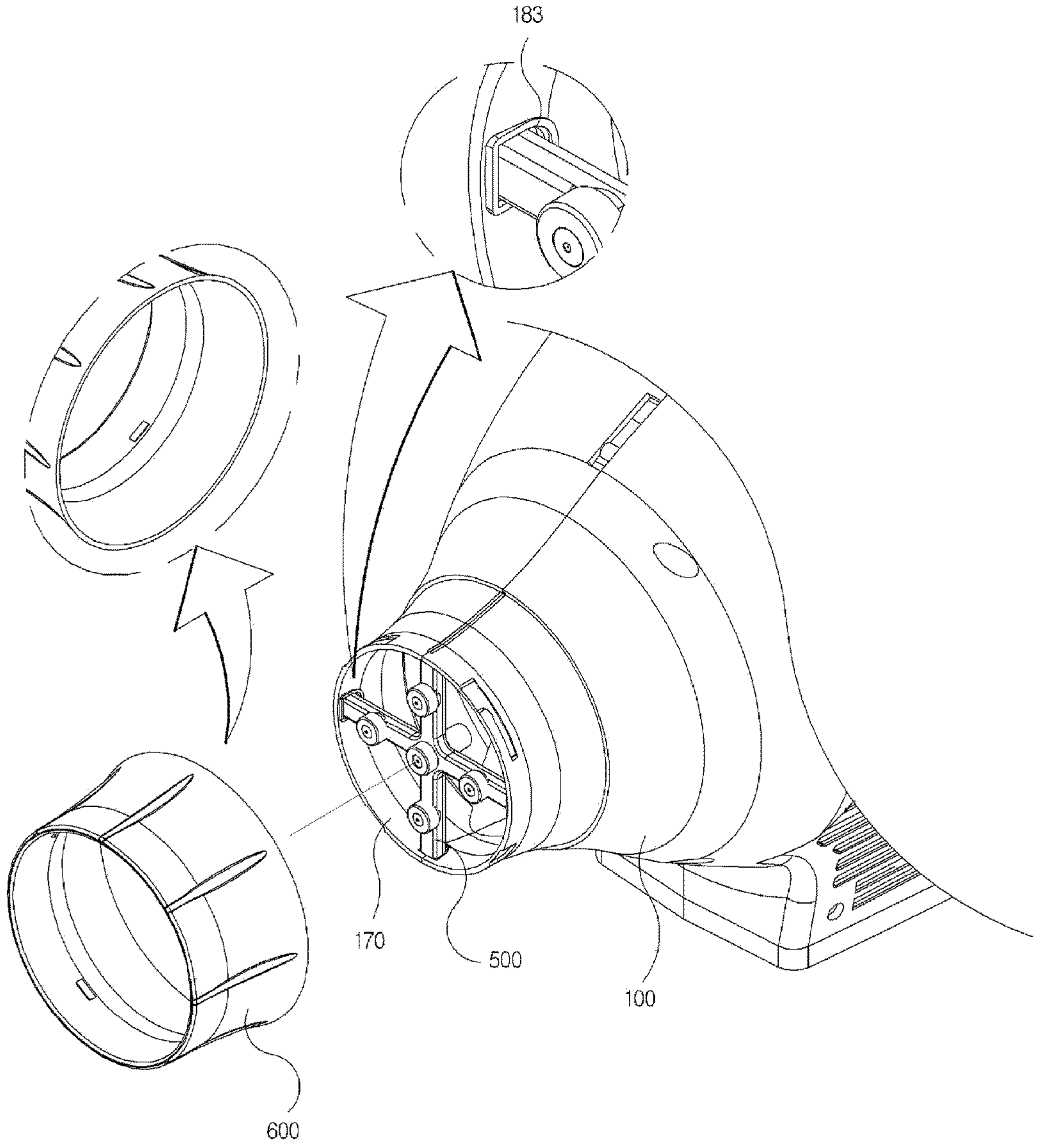

【FIG. 7】
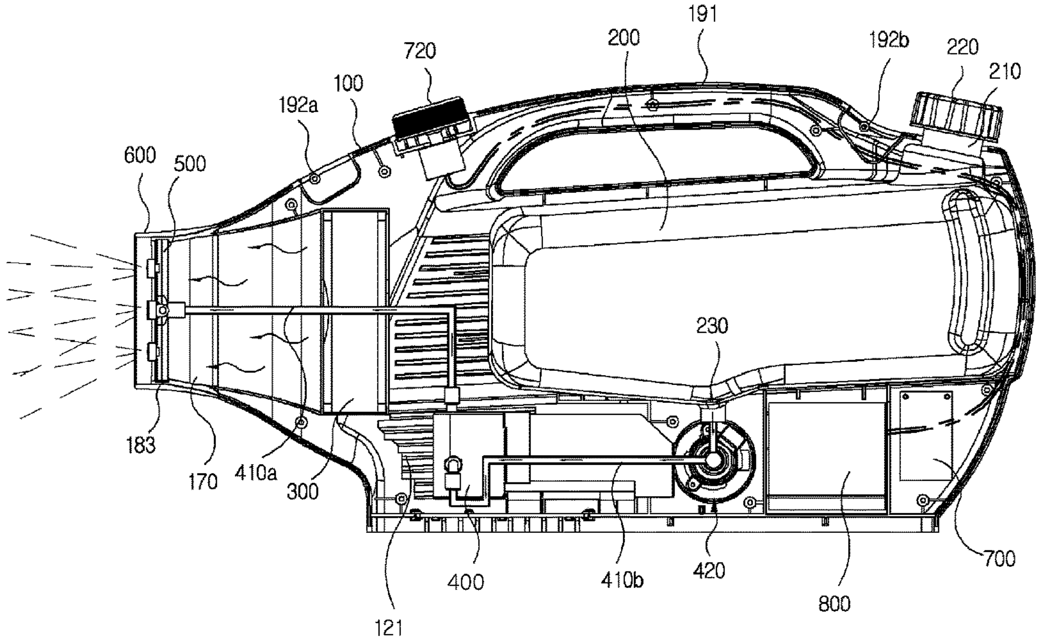

【FIG. 8】
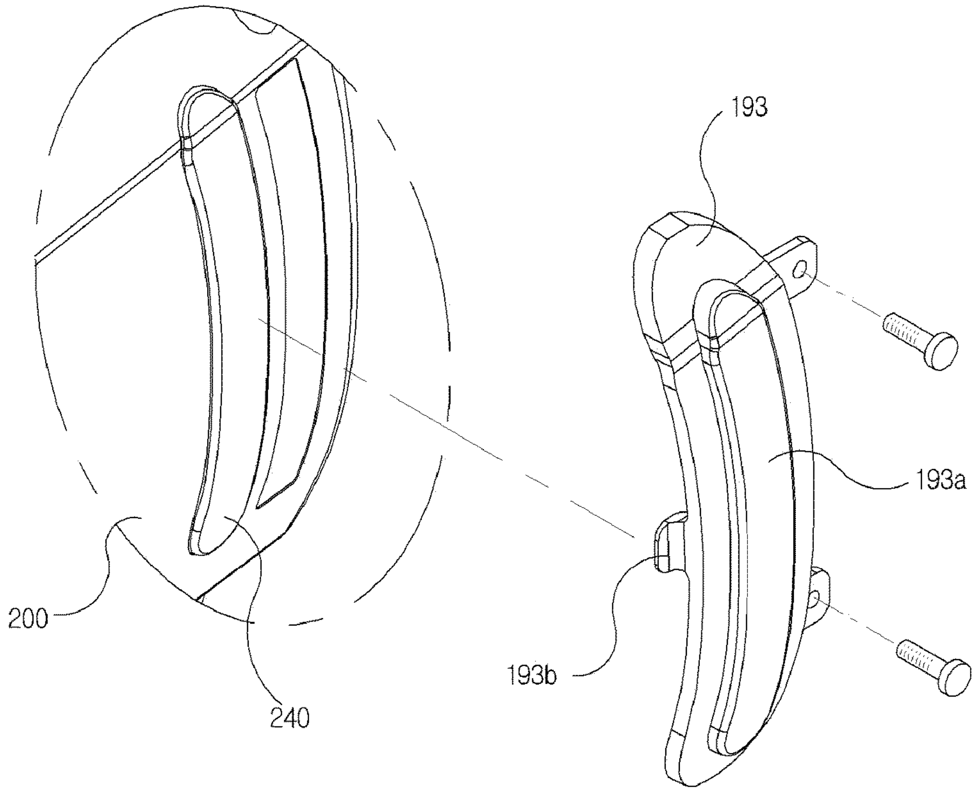

【FIG. 9】
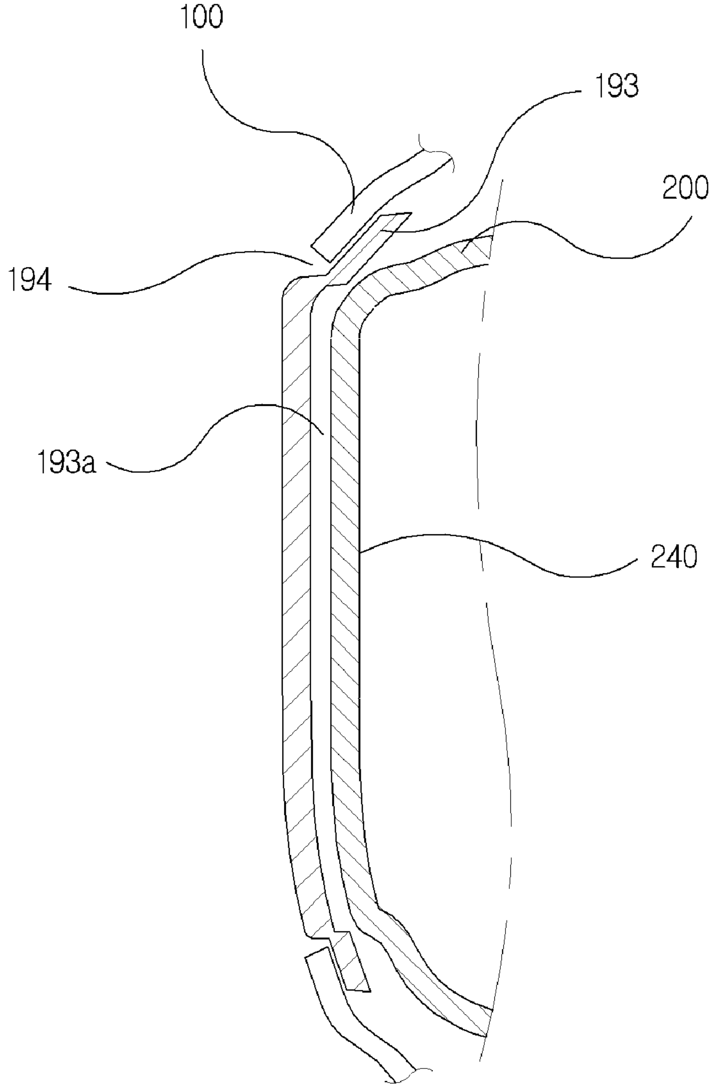

【FIG. 10】
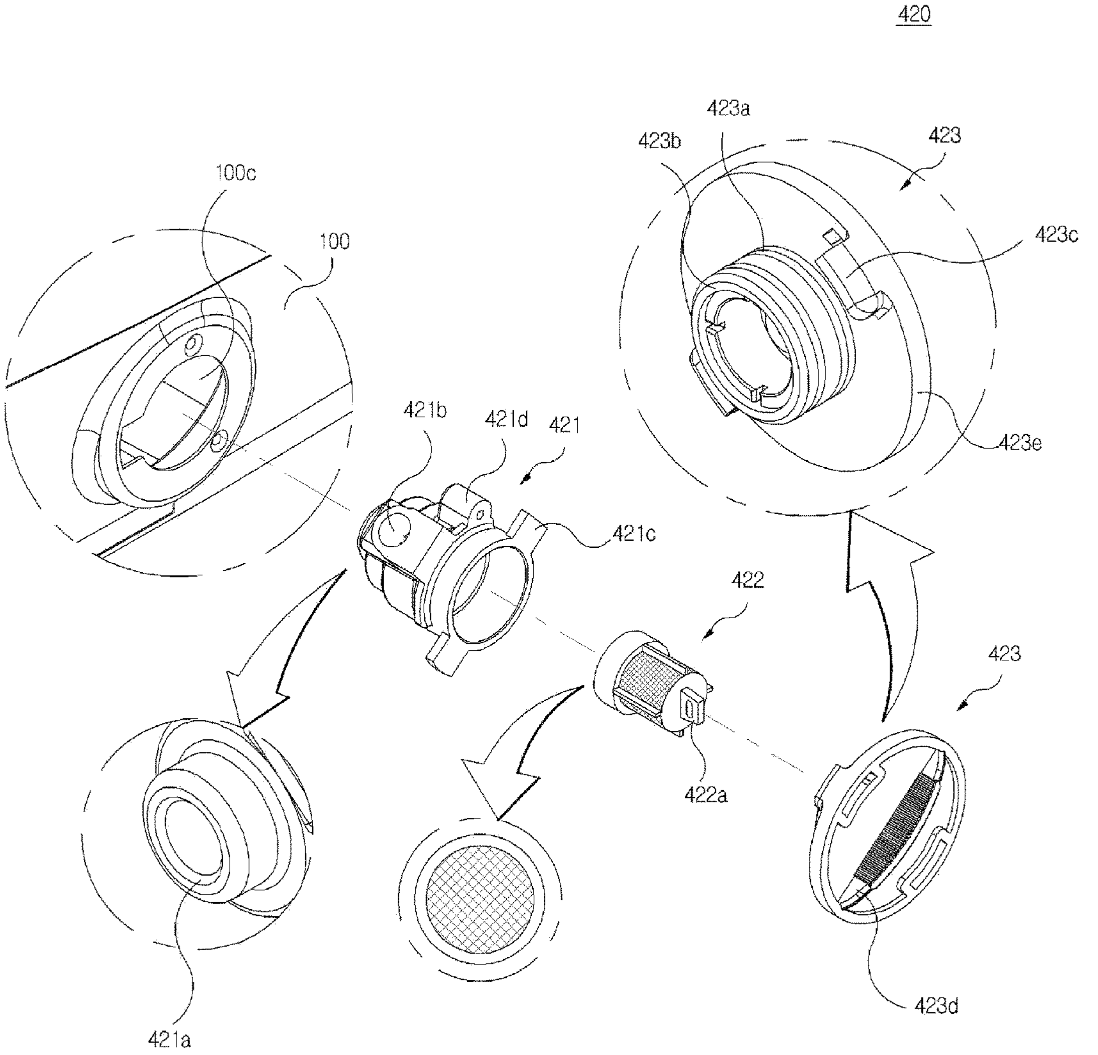

【FIG. 11】
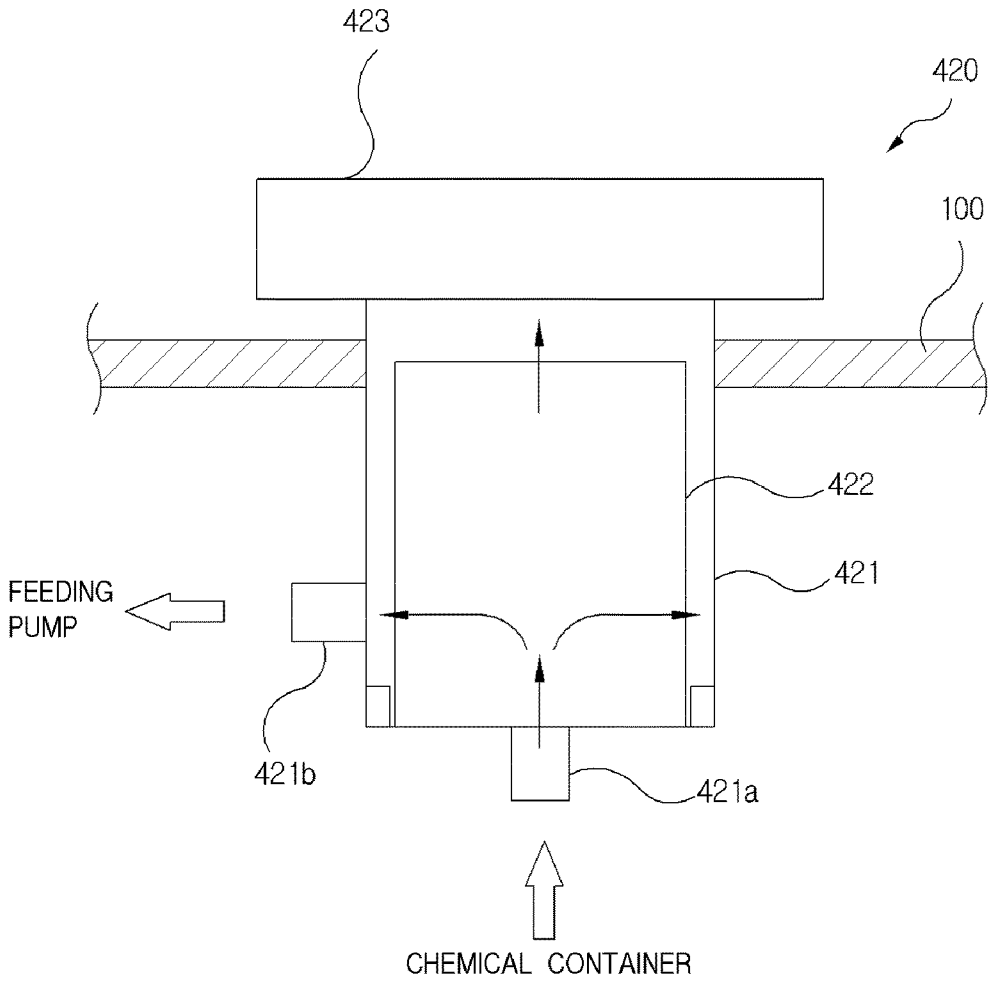

【FIG. 12】
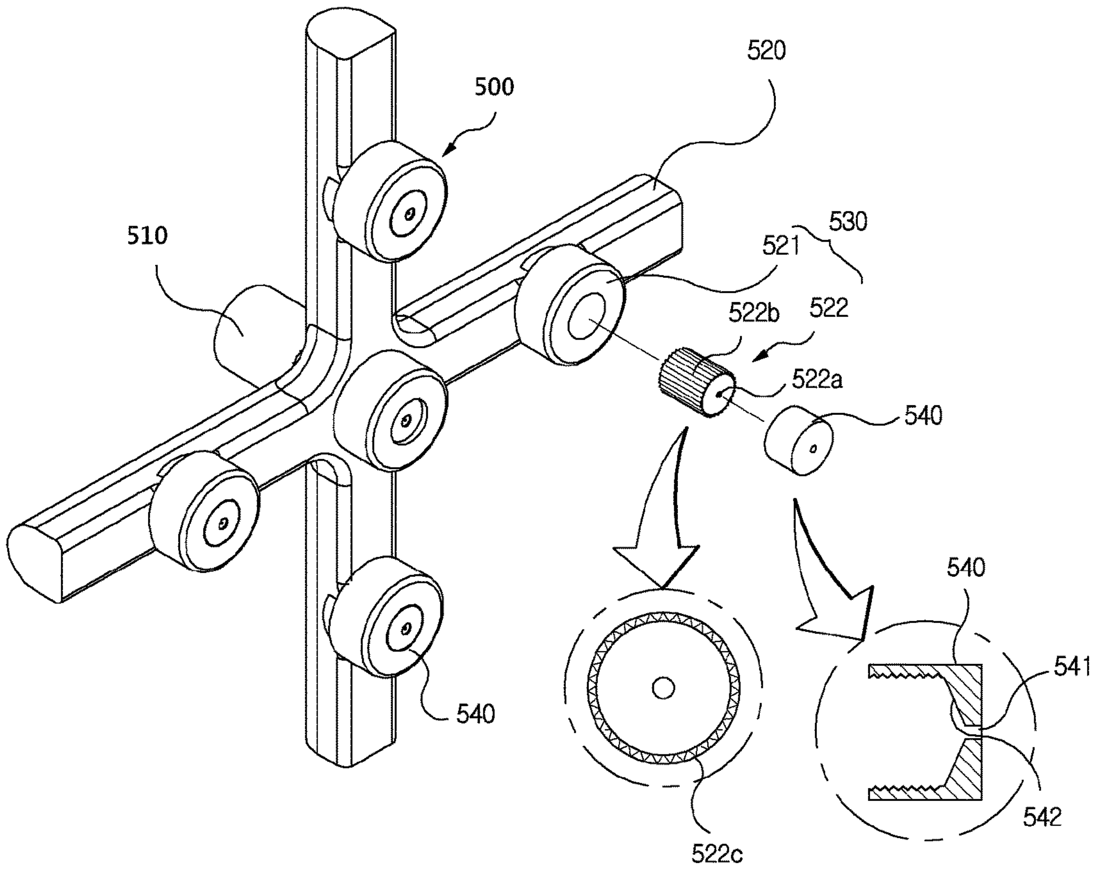

【FIG. 13】
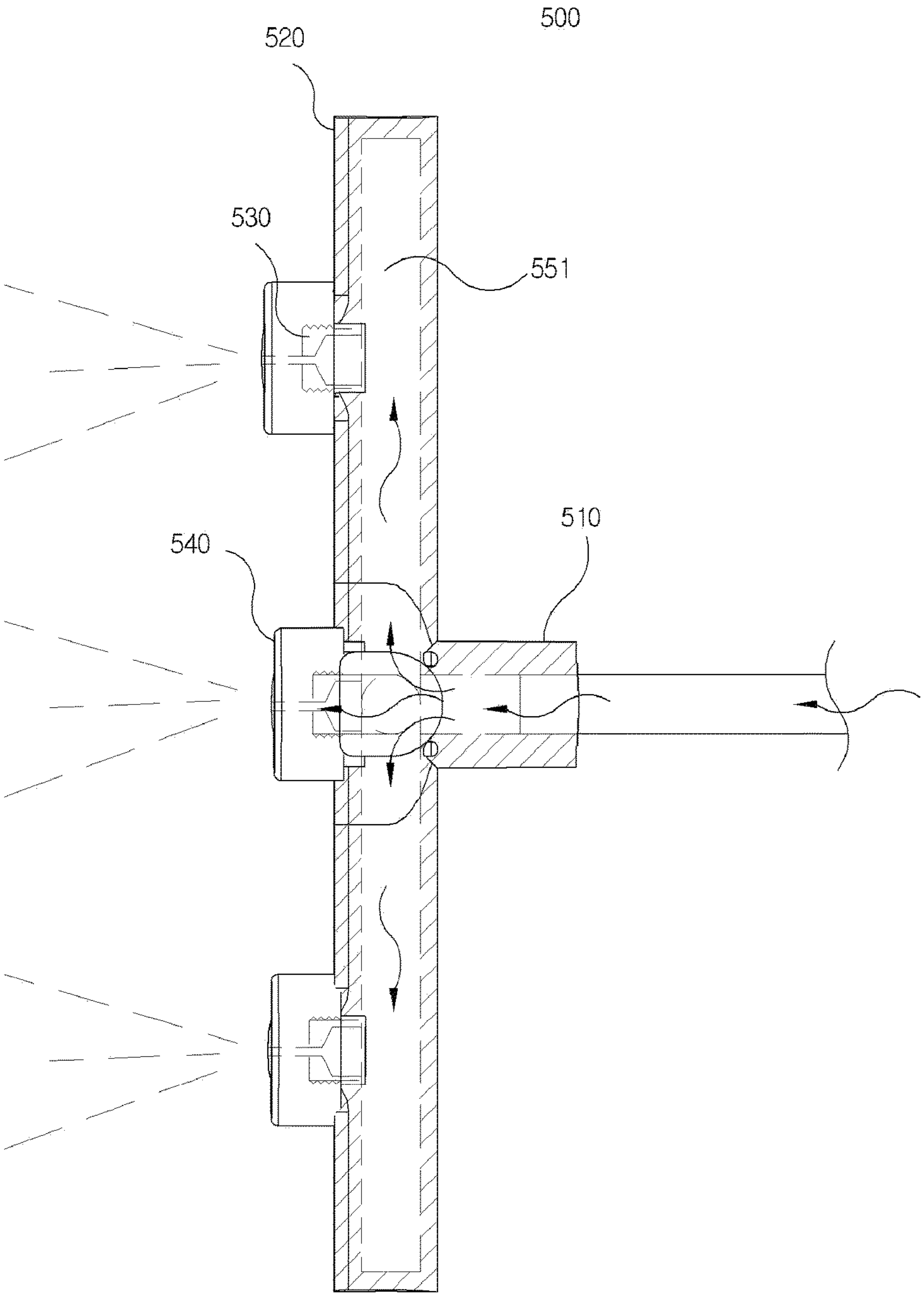

SPRAYER

CROSS-REFERENCE TO RELATED APPLICATIONS

This application claims priority under 35 U.S.C. §119 to Korean Patent Application No. 10-2016-0119039 filed Sep. 19, 2016, in the Korean Intellectual Property Office, the entire contents of which are hereby incorporated by reference.

BACKGROUND

Embodiments of the inventive concept described herein relate to a sprayer, and more particularly, to a sprayer by which an ejection distance of a chemical may be adjusted and internal elements thereof may be easily assembled.

Sprayers that spray a liquid by applying a pressure to the liquid to a wide area may be variously classified according to operation methods, purposes, and sizes thereof. That is, because the sizes, forms, and spraying areas of the particles of mist phases or granular phases have to be various according to purposes such as a domestic purpose, an agricultural purpose, and an industrial purpose, various forms of sprayers are required.

Meanwhile, because it is advantageous to uniformly spray a chemical to wiser areas in an aspect of epidemic prevention in the case of a sprayer for epidemic prevention or sterilization, the sprayers that spray particles having the sizes of several tens or hundreds of micrometers are preferred.

As described above, the sprayers mainly used for epidemic prevention or sterilization are also called chemical sprayers, an epidemic preventer, or a sterilizer. In this way, the prior technologies related to sprayers or spraying apparatuses mainly used epidemic prevention or sterilization include Korean Patent No. 10-1153188 (entitled "Chemical Ejection Apparatus"), Korean Patent No. 10-1185064 (entitled "Chemical Ejection Nozzle"), Korean Patent No. 10-1079206 (entitled "Vortex Forming Member for Chemical Ejection Nozzle").

FIG. 1 is a view illustrating a structure of a chemical ejection apparatus according to the related art. In the conventional chemical ejection apparatus of FIG. 1, air generated when a blowing fan 20 installed in the interior of a body 12 is driven is converted into a high pressure state while passing through a narrow passage 24 provided on a rear side of an air nozzle 22, and most of the air of high pressure is discharged to the outside through an air nozzle 22 whereas some air is supplied to an upper side of a chemical container 30 along a chemical container pressing pipe 26. As a pressure of a space above the surface of water is increased by supplying air of high pressure to an upper side of the water surface of the liquid filled in the chemical container 30 though the chemical container pressing pipe 26, the chemical is discharged to the outside of the chemical container 30 along a chemical pumping pipe 32, of which a lower end is connected to a lower portion of the chemical container 30, and the chemical discharged from the chemical container 30 flows to a chemical nozzle 36 along a chemical discharge pipe 34 connected to the chemical pumping pipe 32. Meanwhile, the air nozzle 22 that discharges air of high pressure supplied from the blowing fan 20 is formed around the chemical nozzle 26 as described above, the chemical discharged through the chemical nozzle 36 is influenced by the air of high pressure discharged from the air nozzle 22 so that mist particles are sprayed.

In order to spray the chemical in the interior of the chemical container 30 through the chemical nozzle 36 by using the principle, a separate pipe connector 40 or organically connecting the chemical container pressing pipe 26, the chemical pumping pipe 32, and the chemical supply pipe 34 in the interior of the chemical ejection apparatus 10 has to be installed in a section in which the body 12 and the chemical container 30 are assembled. Further, a chemical adjusting unit 38 for adjusting the ejected chemical has to be installed in the chemical discharge pipe 34, and an assembling unit 50 for maintaining the assembled state of the body 12 and the chemical container 30 while the pipe connector 40 is interposed between the body 12 and the chemical container 30 may be provided.

In the conventional chemical ejection apparatus, a pressure generated on a rear side of the nozzle through driving of the blowing fan is partially delivered to the chemical container, the chemical in the chemical container is pumped by the air of high pressure delivered to the chemical container, a plurality of pipes have to be arranged in the interior of the body for a series of processes for spraying the chemical through the chemical nozzle, and a separate apparatus for adjusting the chemical in the chemical discharge pipe has to be also provided, which makes the structure of the chemical spraying apparatus complex.

SUMMARY

Embodiments of the inventive concept provide a sprayer by which initiation of ejection of a chemical, an amount of the ejected chemical, and an ejection distance of the chemical may be accurately adjusted and internal elements thereof may be easily assembled.

The inventive concept has the following configurations to solve the above-mentioned objects.

In accordance with an aspect of the inventive concept, there is provided a sprayer including a body which includes a pair of housings that is transversely separated from and coupled to each other, in which a chemical container assembly, a blower module assembly, a feeding pump assembly, and an ejection nozzle assembly are provided in the interior thereof, in which a suction hole is formed on a rear side of the blower module assembly, and which has a neck, of which an inner sectional area becomes gradually smaller as it goes towards a front side, on a front side of the blower module assembly, a chemical container that includes a chemical injection hole that is installed at an upper portion thereof to be exposed to the outside of the body, a chemical container top which has an air hole for flows of air to the outside in the chemical injection hole and which has a check valve in the interior thereof such that the chemical injection hole is opened and closed, and a chemical discharge hole that is formed at a lower portion thereof, a blower module that is installed in the blower module assembly of the body such that exterior air is suctioned into the body and is discharged to the outside through the neck, a feeding pump that is installed in the pump assembly of the body and is connected to the chemical discharge hole of the chemical container by a connection pipe, an ejection nozzle assembly that is installed in the ejection nozzle assembly of the body to be connected to the feeding pump by a connection pipe, and a tube-shaped fixing cap, of which a front side and a rear side are opened, are separated from and coupled to an end of the neck of the body.

Each of the chemical container assembly, the blower module assembly, the pump assembly, and the ejection nozzle assembly may include at least one of a partition wall, a rib, and a coupling recess.

The body may include a grip handle or a connection ring for coupling with a ring of a suspender.

A display window of a transparent or translucent material may protrude vertically from the chemical container, and the body may have a scale window at a location corresponding to the display window of the chemical container.

The scale window may have a coupling recess corresponding to the display window, and may be separated from and coupled to a cutaway recess that is formed in the body.

The scale window may be coupled to to the cutaway recess of the body through screw coupling or ultrasonic fusion.

A push boss that pushes a side surface of the chemical container may be formed inwards on one side of the scale window.

The sprayer may further include a filter module that is provided in a connection pipe that connects the chemical container and the feeding pump, and the filter module includes a filter fixing member that includes an inlet hole that is connected to the chemical container, an outlet hole that is connected to the feeding pump, and a coupling boss that is formed outwards, is installed in the body, and has an interior space, of which one side is opened such that a portion thereof is exposed to the outside, a filter that has a tube shape, of which one side is opened, and is installed in an interior of the filter fixing member to be coupled to the inlet hole, and a fixing cap that has a closed cylinder for opening and closing an interior space opening part of the filter fixing member on an inner surface thereof, has a coupling boss that is paired with the coupling boss at an outer side of the closed cylinder, and has a handle on an outer surface thereof.

The fixing cap may be configured such that an O-ring is coupled to an outer peripheral surface of the closed cylinder.

A battery assembly may be provided in an interior space of the body, a battery may be inserted into the battery assembly and may be connected to a control circuit panel that controls driving of the sprayer, and a power connector may be connected to the battery to charge an external power source.

The sprayer may further include a control knob that is connected to the control circuit panel to adjust a rotational speed of a driving motor of the blower module, and a portion of the control knob may be coupled to the body such a portion thereof is exposed to the outside.

The control circuit panel may turn on and off the feeding pump and the driving motor of the blower module simultaneously in conjunction with driving of the control knob and may control the rotational speed of the driving motor of the blower module.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIG. 1 is a view illustrating a structure of a chemical ejection apparatus according to the related art;

FIG. 2 is a perspective view of a sprayer according to an embodiment of the inventive concept;

FIG. 3 is an exploded perspective view of the sprayer according to the embodiment of the inventive concept;

FIG. 4 is a view illustrating a coupling structure of a chemical injection hole and a chemical top of FIGS. 2 and 3;

FIGS. 5A and 5B are sectional views illustrating a suction hole of FIGS. 2 and 3;

FIG. 6 is a perspective view illustrating a coupling structure of an ejection nozzle assembly and a body of FIGS. 2 and 3;

FIG. 7 is a view illustrating an internal structure of the sprayer according to the embodiment of the inventive concept;

FIGS. 8 and 9 are an exploded perspective view and a sectional view illustrating a coupling structure of main parts of the chemical container and the body of FIGS. 2 to 7;

FIGS. 10 and 11 are an exploded perspective view and a sectional view of a filter module of FIGS. 2 to 7;

FIG. 12 is a perspective view of the ejection nozzle assembly of FIGS. 2 to 7; and FIG. 13 is a view of the interior of the ejection nozzle assembly 500 of FIG. 11.

DETAILED DESCRIPTION

Hereinafter, a configuration and an operation of a sprayer according to an embodiment of the inventive concept will be described with reference to the accompanying drawings.

FIG. 2 is a perspective view of a sprayer according to an embodiment of the inventive concept. FIG. 3 is an exploded perspective view of the sprayer according to the embodiment of the inventive concept. FIG. 4 is a view illustrating a coupling structure of a chemical injection hole and a chemical top of FIGS. 2 and 3. FIGS. 5A and 5B are sectional views illustrating a suction hole of FIGS. 2 and 3. FIG. 6 is a perspective view illustrating a coupling structure of an ejection nozzle assembly and a body of FIGS. 2 and 3. FIG. 7 is a view illustrating an internal structure of the sprayer according to the embodiment of the inventive concept.

As illustrated in FIGS. 2 to 7, the sprayer according to the embodiment of the inventive concept includes a body 100 that includes a pair of housings 100*a* and 100*b*, a chemical container 200 that accommodates a chemical, a blower module 300 that includes a driving motor and a blowing fan, a feeding pump 400 that pumps the chemical, an ejection nozzle assembly 500 that includes five ejection nozzles 530, a fixing cap 600, of which opposite sides are opened, a control circuit panel 700 that includes a circuit for controlling driving of the sprayer including the blower module 300 and the feeding pump 400, and a battery 800 for charging electric power.

Among the elements, the body 100 that is a frame of the sprayer is an injection-molded product that includes the pair of housings 100*a* and 100*b*, which are separated from and coupled to each other transversely while the elements including the chemical container 200 are inserted within the body 100, and has a transversely symmetrical structure for simplification of the structure of the injection-molding mold and an easy assembly of the body 100.

The pair of housings 100*a* and 100*b* may be coupled to each other while being integrally assembled. Further, a front side of the pair of housings 100*a* and 100*b*, that is, a neck 170 of the body 100 are coupled with a fixing cap 600 that has a structure of which a diameter becomes smaller as it goes forwards.

A chemical container assembly 110, a blower module assembly 120, a pump assembly 130, an ejection module assembly 140, a battery assembly 150, and a control circuit assembly 160 are provided in an interior space of the body 100, a suction hole 121 through which exterior air is suctioned is formed in the housings 100*a* and 100*b* at a rear part of the blower module assembly 120, and a neck of which an inner sectional area becomes gradually smaller as it goes to the front side and of which a front side is opened is formed at a front part of the blower module assembly 120.

Here, as the suction hole 121 is formed by a grill 121*a* that is formed in the body 100 to be stepped such that an outside of the body 100 is lower than an inside of the body 100 as in FIG. 5A or is formed by a grill 121*b* that is is inclined such that the outside of the body 100 is lower than the inside of the body 100 as in FIG. 5B, exterior air A is smoothly suctioned into the interior of the body 100 but foreign substances W such as water is blocked by the grills 121*a* and 121*b* to be prevented from being introduced into the interior of the body 100.

The chemical container assembly 110, the blower module assembly 120, the pump assembly 130, the ejection nozzle assembly 140, the battery assembly 150, and the control circuit assembly 160 in the body 100, that is, the housings 100*a* and 100*b* are partitioned by a partition wall 181, a rib 182, and coupling recesses 183.

Here, the partition wall 181 is formed vertically or horizontally on inner surfaces of the housings 1001 and 100*b* to vertically and horizontally divide the interior spaces of the housings 100*a* and 100*b* such that the chemical container 200, the blower module 300, the pump 400, the ejection nozzle assembly 500, the battery 800, and the control circuit panel 700 may be received in the divided spaces. Further, the rib 182 is formed horizontally on the inner surfaces of the housings 100*a* and 100*b* to support side surfaces or front and rear surfaces of the chemical container 200, the blower module 300, the pump 400, the ejection nozzle assembly 500, the battery 800, and the control circuit panel 700 assembled in the chemical container assembly 110, the blower module assembly 120, the pump assembly 130, the ejection nozzle assembly 140, the battery assembly 150, and the control circuit assembly 160. Further, the coupling recesses 183 are formed in the housings 100*a* and 100*b* that constitute the pump assembly 130 or the ejection nozzle assembly 140 directly or by using a separate rib to provide a recess part to which a portion of the pump 400 or the ejection nozzle assembly 500 may be coupled.

The chemical container 200 assembled in the chemical container assembly 110 of the body 100 is a container for storing a chemical, and is configured such that a chemical injection hole 210 is formed at an upper portion thereof to be exposed to the outside of the body 100 and a chemical discharge hole 230 through which the chemical is discharged is formed at a lower portion thereof. The chemical container top 220 is screw-coupled to the chemical injection hole 210 such that the chemical injection hole 210 is opened and closed, and an air hole 221 for flows of air to the outside of the chemical container 200 is formed in the chemical top 220 and a check valve 222, with which the air hole 221 is communicated, is installed in the interior of the chemical container top 220. The check valve 222 passes air introduced into the interior of the chemical container 200, but prevents the chemical stored in the chemical container 200 from being leaked to the outside.

Further, the blower module 300 assembled in the blower module assembly 120 of the body 100 includes a driving motor and a blowing fan, and is installed in the blower module assembly 120 of the body 100 to suction exterior air into the interior of the body 100 and discharge the exterior air together with the chemical through the neck 170. Further, opposite ends of the feeding pump 400 assembled in the feeding pump assembly 130 of the body 100 are connected to the chemical discharge hole 230 of the chemical container 200 and the ejection nozzle assembly 50 by connection pipes 410*a* and 410*b*, respectively, to pump the chemical in the chemical container 200 to the ejection nozzle assembly 500.

Then, as the chemical container 200, the pump 400, and the ejection nozzle assembly 500, and the connection pipes 410*a* and 410*b* are connected to each other by connection members having various shapes, the connection operations may be easily performed and deformation of the connection pipes 410*a* and 410*b* may be restrained during or after the connection processes so that the chemical may flow smoothly.

Further, the ejection nozzle assembly 500, by which the chemical is ejected, is installed in the ejection nozzle assembly 140 of the body, that is, in the interior of the neck 170 such that the feeding pump 400 and the connection pipe 410*a* are connected to each other. To achieve this, the coupling recesses 183 that may accommodate ends of the ejection nozzle assembly 500 may be formed on the upper, lower, left and right sides of the neck 170 of the housings 100*a* and 100*b*.

Then, the coupling recesses 183 formed on the left and right sides of the neck 170 of the housings 100*a* and 100*b* are perfect entities, and the coupling recesses 183 formed on the upper and lower sides of the neck 170 are half entities and constitute a perfect entity through coupling of the housings 100*a* and 100*b*.

The fixing cap 600 has a tube shape, of which front and rear sides are opened, and is coupled to an end of the neck 170 of the body 100 to integrally couple the pair of housings 100*a* and 100*b* and guide the chemical and air such that the chemical and the air are ejected in a specific direction.

Further, connection rings 192*a* and 192*b*, together with a grip handle 191 for carrying the sprayer, may be provided at upper portions of the body 100, and is provided for coupling with a suspender by which the user may suspend the sprayer on his or her shoulder.

FIGS. 8 and 9 are an exploded perspective view and a sectional view illustrating a coupling structure of main parts of the chemical container and the body of FIGS. 2 to 7.

As illustrated in FIGS. 7 and 9, the body 100 and the chemical container 200 include a scale window 193 and a display window 240, which are transparent or translucent, by which the user may visually verify a level of the chemical stored in the chemical container 200 from the outside of the body 100.

The scale window 193 and the display window 240 protrude to the outside further than the body 100 and the chemical container 200, had have lengths corresponding to a distance between an upper and a lower end of the chemical container 200. In particular, the scale window 193 of the body 100 and the display window 240 of the chemical container 200 have structures that may overlap each other to be attached to each other.

However, because the housings 100*a* and 100*b* of the body 100 are formed of an opaque material, a cutaway recess corresponding to the display window 240 is formed in the body 100 to install the display window 240 in the body 100 and the display window 240 is formed as a separate component to be coupled to the cutaway recess 194.

In this way, the display window 240 formed as a separate component from the body 100 has a coupling recess 193*a*, to which the scale window 193 of the chemical container 200 is coupled, on an inner surface thereof, and a periphery of the display window 240 extends with a specific width such that the display window 240 is prevented from being withdrawn to the outside when it is coupled to the cutaway recess 194 of the body 100.

In particular, one or more push bosses 193*b* are formed inwards on one side of the scale window 193, and function to push a side surface of the chemical container 200 such that the chemical container 200 is prevented from being moved within the body 100 in a process of ejecting the chemical when the chemical container 200 is assembled in the body 100.

In this way, the scale window 193 coupled to the cutaway recesses 194 of the body 100 is fixed to the body 100 through screw coupling, ultrasonic fusion, or various adhesives.

Although it has been described as an example that a scale for displaying the level of the chemical stored in the chemical container 200 is formed in the scale window 193, that is, in the body 100, the inventive concept is not limited thereto and the same effect may be achieved even though the scale is formed in the display window 240, that is, in the chemical container 200.

FIGS. 10 and 11 are an exploded perspective view and a sectional view of a filter module 420 that is situated on the connection pipe 410*b* that connects the chemical container 200 and the feeding pump 400 of FIGS. 2 to 7.

In this way, the filter module 420 as illustrated in FIGS. 10 and 11 is provided on the connection pipe 410*b* that connects the chemical container 200 and the feeding pump 400 to block flows of various foreign substances contained in the chemical, and includes a filter fixing member 421, a filter 422, and a fixing cap 423.

The filter fixing member 421 is fixed to the body 100 through screw coupling or the like as a portion thereof is assembled in a coupling hole 100*c* of the body 100 to be exposed to the outside, and one end of the filter fixing member 421 is opened and an inlet hole 421*a* for connection with the chemical container 200 is formed at an opposite side thereof, and a side surface thereof has a cylindrical shape having an outlet hole 421*b* for connection with the feeding pump 400. The filter fixing member 421 has a coupling boss 421*c* for coupled to the fixing cap 423 at an end portion thereof, that is, at a portion thereof exposed to the outside of the body 100, and a fixing boss 421*d* is formed to be spaced apart from the coupling boss 421*c* at a specific gap, that is, a gap that is larger than the thickness of the body 100.

The fixing boss 421*c* and the fixing boss 421*d* are two or more bosses that are arranged horizontally, and are situated outside and inside the body 100, respectively, when being coupled to the body 100, to fix the filter fixing member 421 to the body 100 or to be coupled to the fixing cap 423.

One side and a side surface of the filter 422 coupled to the interior of the filter fixing member 421 include a net and an opposite side thereof has an opened tube shape, and various foreign substances contained in the chemical that is introduced through the inlet hole 421*a* and discharged through the outlet hole 421*b* may be filtered by blocking the inlet hole 421*a* and the outlet hole 421*b* with nets as the filter 422 is coupled to the interior of the fixing member 421 such that an opened side thereof faces the inside.

Then, a handle 422*a* for separating and coupling the filter 422 is formed one side of the filter 422.

The fixing cap 423 that is separated from and coupled to the opened side of the filter fixing member 421 includes a disk-shaped cap body 423*e*, a closed cylinder 423*b* that is formed on an inner surface of the cap body 423*e* to open and close the opened side of the filter fixing member 421, a coupling boss 423*c* that is formed on an inner surface of the cap body 423*e* to correspond to the coupling boss 421*c* of the filter fixing member 421 while being spaced apart from the closed cylinder 423*b* at a specific gap, and an opening/closing handle 423*d* formed on an outer surface of the cap body 423*e*.

In particular, as an O-ring 423*a* is coupled to an outer peripheral surface of the closed cylinder 423*b*, an outer peripheral surface of the closed cylinder 423*b* of the fixing cap 423 is attached to an inner surface of the filter fixing member 421 when the fixing cap 423 is coupled to the filter fixing member 421 so that the chemical that passes via the filter module 420 is prevented from being leaked.

FIG. 12 is a perspective view of the ejection nozzle assembly 500 of FIGS. 2 to 7. FIG. 13 is a view of the interior of the ejection nozzle assembly 500 of FIG. 11.

As illustrated in FIGS. 11 and 12, the ejection nozzle assembly 500 includes a connector 510 that is connected to the chemical container, that is, to the feeding pump, a branch pipe 520 that is branched from one end of the connector 510 into cross shapes while forming the right angle with the connector 510, ejection nozzles 530 that are arranged in the branch type 520 at a specific interval, and a fixing cap 540 that is formed at a front end of the ejection nozzle 530 to be separated and coupled.

In this way, the connector 510 and the branch pipe 520 are integrally injection-molded, and a passage 551 for flows of the chemical is formed in the interior of the connector 510 and the branch pipe 520. The opened passage 551 of the end of the branch pipe 520 is closed through a separate finishing operation after the injection-molding.

Five ejection nozzles 530 are provided in the branch pipe 520, and each of the ejection nozzles 530 includes a fixing tube 521 that is formed to face a front side of the branch pipe 520, and a cylindrical fixing body 522 that has a nozzle hole 522*a* at the center thereof and a spiral portion 522*b* on an outer peripheral surface thereof and that is inserted into the fixing tube 521. Accordingly, as the fixing body 522 is integrally coupled o the fixing plate 521, ejection holes 522*a* and 522*c* for ejecting the chemical are formed at the center of the fixing body 522 and between the fixing body 522 and the fixing plate 521.

Further, the fixing cap 540 is coupled to the fixing tube 521, and as a through-hole 541 is formed at the center of the fixing cap 540 and an inclined surface 542 is formed at a periphery of the through-hole 541, that is, an inner surface of the through hole 541 such that it becomes thicker as it becomes far from the through-hole 541, the chemical ejected from the ejection hole 522*a* is ejected to the front side through the through-hole 541 and the chemical ejected through the ejection hole 522*c* is sprayed at a specific angle through the through-hole 541 while flowing along the inclined surface 542.

Further, as illustrated in FIGS. 2 to 7, in the sprayer according to the embodiment of the inventive concept, as the battery assembly 150 is provided in the interior space of the body 100, a rechargeable battery 800 is inserted into the battery assembly 150 to be connected to the control circuit panel 700 that controls driving of the sprayer, and a power connector 710 is connected to the battery 800 such that the battery charges an external power source, driving of the sprayer may be controlled and electric power that is necessary for driving of the sprayer may be changed as well.

Further, as illustrated in FIGS. 2 to 7, in the sprayer according to the embodiment of the inventive concept, as a portion of a control knob 720 connected to the control circuit panel 700 is coupled to the body 100 to be exposed to the outside of the body 100, an ejection distance of the chemical may be easily adjusted by adjusting a rotational speed of the driving motor that constitutes the blower module 300.

Here, the control circuit panel 700 may turn on and off the feeding pump 400 and the driving motor of the blower module 300 in conjunction with driving (rotation) of the control knob 720, and may freely control a rotational speed of the driving motor of the blower module 300.

Until now, some embodiments of the sprayer according to the inventive concept have been described with reference to the accompanying drawings. The embodiments pertain to the technical spirit that is claimed in the claims of the inventive concept. Further, the embodiments are simply exemplary, and should not be construed to limit the scope of the claims.

According to the inventive concept, the sprayer may be easily carried and perform an ejection operation easily, initiation of ejection of a chemical, an amount of the ejected chemical, and an ejection distance of the chemical may be accurately adjusted, and internal elements of the sprayer may be easily assembled.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A sprayer comprising:

a body which comprises a pair of housings that are transversely separated from and coupled to each other, in which a chemical container assembly, a blower module assembly, a feeding pump assembly, and an ejection nozzle assembly are provided in the interior thereof, in which a suction hole is formed on a rear side of the blower module assembly, and which has a neck, of which an inner sectional area becomes gradually smaller as it goes towards a front side, on a front side of the blower module assembly;

a chemical container that comprises a chemical injection hole that is installed at an upper portion thereof to be exposed to the outside of the body, a chemical container top which has an air hole for flows of air to the outside in the chemical injection hole and which has a check valve in the interior thereof such that the chemical injection hole is opened and closed, and a chemical discharge hole that is formed at a lower portion thereof;

a blower module that is installed in the blower module assembly of the body such that exterior air is suctioned into the body and is discharged to the outside through the neck;

a feeding pump that is installed in the pump assembly of the body and is connected to the chemical discharge hole of the chemical container by a connection pipe;

an ejection nozzle assembly that is installed in the ejection nozzle assembly of the body to be connected to the feeding pump by a connection pipe; and a tube-shaped fixing cap, of which a front side and a rear side are opened, separated from and coupled to an end of the neck of the body.

2. The sprayer of claim 1, wherein each of the chemical container assembly, the blower module assembly, the pump assembly, and the ejection nozzle assembly of the body comprises at least one of a partition wall, a rib, and a coupling recess.

3. The sprayer of claim 1, wherein the body comprises a grip handle or a connection ring for coupling with a ring of a suspender.

4. The sprayer of claim 1, wherein a display window of a transparent or translucent material protrudes vertically from the chemical container, and the body has a scale window at a location corresponding to the display window of the chemical container.

5. The sprayer of claim 4, wherein the scale window has a coupling recess corresponding to the display window, and is separated from and coupled to a cutaway recess that is formed in the body.

6. The sprayer of claim 5, wherein the scale window is coupled to to the cutaway recess of the body through screw coupling or ultrasonic fusion.

7. The sprayer of claim 4, wherein a push boss that pushes a side surface of the chemical container is formed inwards on one side of the scale window.

8. The sprayer of claim 1, further comprising:

a filter module connected to the connection pipe that connects the chemical container and the feeding pump, wherein the filter module comprises:

a filter fixing member that comprises an inlet hole that is connected to the chemical container, an outlet hole that is connected to the feeding pump, and a coupling boss that is formed outwards, is installed in the body, and has an interior space, of which one side is opened such that a portion thereof is exposed to the outside;

a filter that has a tube shape, of which one side is opened, and is installed in an interior of the filter fixing member to be coupled to the inlet hole; and a fixing cap that has a closed cylinder for opening and closing an interior space opening part of the filter fixing member on an inner surface thereof, has a coupling boss that is paired with the coupling boss at an outer side of the closed cylinder, and has a handle on an outer surface thereof.

9. The sprayer of claim 8, wherein the fixing cap is configured such that an O-ring is coupled to an outer peripheral surface of the closed cylinder.

10. The sprayer of claim 1, wherein a battery assembly is provided in an interior space of the body, a battery is inserted into the battery assembly and is connected to a control circuit panel that controls driving of the sprayer, and a power connector is connected to the battery to charge the battery with an external power source.

11. The sprayer of claim 10, further comprising:

a control knob that is connected to the control circuit panel to adjust a rotational speed of a driving motor of the blower module, wherein a portion of the control knob is coupled to the body such a portion thereof is exposed to the outside.

12. The sprayer of claim 11, wherein the control circuit panel turns on and off the feeding pump and the driving motor of the blower module simultaneously, in conjunction with adjusting the rotational speed of the driving motor of the blower module.

* * * * *